(12) United States Patent
Zhou et al.

(10) Patent No.: US 9,775,794 B2
(45) Date of Patent: Oct. 3, 2017

(54) USE OF GELATIN OR DEEPLY PROCESSED GELATIN MATERIALS IN PREPARATION OF HAIR QUALITY-IMPROVING COMPOSITIONS

(71) Applicant: DONG-E E-JIAO CO., LTD, Liaocheng (CN)

(72) Inventors: Xiangshan Zhou, Liaocheng (CN); Jinhua You, Liaocheng (CN); Shousheng Tian, Liaocheng (CN); Chuanliang Ji, Liaocheng (CN); Yan Zhang, Liaocheng (CN); Chunyan Wang, Liaocheng (CN); Lu Zhang, Liaocheng (CN); Min Li, Liaocheng (CN); Shidong Li, Liaocheng (CN); Yangen Sun, Liaocheng (CN)

(73) Assignee: DONG-E E-JIAO CO., LTD., Liaocheng (CN)

( * ) Notice: Subject to any disclaimer, the term of this patent is extended or adjusted under 35 U.S.C. 154(b) by 0 days.

(21) Appl. No.: 15/024,381

(22) PCT Filed: Sep. 24, 2014

(86) PCT No.: PCT/CN2014/000868
§ 371 (c)(1),
(2) Date: Mar. 24, 2016

(87) PCT Pub. No.: WO2015/043115
PCT Pub. Date: Apr. 2, 2015

(65) Prior Publication Data
US 2016/0213591 A1    Jul. 28, 2016

(30) Foreign Application Priority Data
Sep. 25, 2013   (CN) .......................... 2013 1 0441560

(51) Int. Cl.
*C12P 21/06* (2006.01)
*A61K 8/65* (2006.01)
*A61K 35/36* (2015.01)
*A61Q 5/00* (2006.01)
*A61Q 7/00* (2006.01)
*C07K 1/36* (2006.01)
*C07K 14/78* (2006.01)

(52) U.S. Cl.
CPC ............... *A61K 8/65* (2013.01); *A61K 35/36* (2013.01); *A61Q 5/00* (2013.01); *A61Q 5/002* (2013.01); *A61Q 7/00* (2013.01); *C07K 1/36* (2013.01); *C07K 14/78* (2013.01); *C12P 21/06* (2013.01)

(58) Field of Classification Search
None
See application file for complete search history.

(56) References Cited

FOREIGN PATENT DOCUMENTS

| CN | 102406591 | 4/2012 |
|----|-----------|--------|
| CN | 103655616 | 3/2014 |

OTHER PUBLICATIONS

Eating Donkey Hide Gelatin for Lustrous Skin? Apr. 19, 2011 pp. 1-22.*
Yang, Fuan et al., Modern Research and Preview on Asini Corii Colla, Chinese Journal of Information on TCM, May 31, 2004, vol. 5, No. 11, p. 467, left column, paragraphs [0002] and [0004] and p. 468, left column, paragraph [0002].
Gao, Jinghui et al., Modern Research Progress on Asini Corii Colla, Chinese Pharmaceutical Affairs, Apr. 30, 2011, vol. 4, No. 25, p. 4396, left column, paragraphs [0001] and [0002] and right column, paragraph [0001].
International Search Report filed in PCT/CN2014/000868 mailed Nov. 26, 2014.

* cited by examiner

*Primary Examiner* — Robert Yamasaki
(74) *Attorney, Agent, or Firm* — Rankin, Hill & Clark LLP (57) ABSTRACT

Disclosed the use of gelatin or deeply processed gelatin materials in the preparation of hair quality-improving compositions.

9 Claims, 5 Drawing Sheets

USE OF GELATIN OR DEEPLY PROCESSED GELATIN MATERIALS IN PREPARATION OF HAIR QUALITY-IMPROVING COMPOSITIONS

CROSS-REFERENCE TO RELATED APPLICATIONS

This application claims the priority of the China Provisional Patent Application No. 201310441560.6 filed on Sep. 25, 2013. The specification of said application is incorporated by reference in its entirety herein.

TECHNICAL FIELD

The present invention relates to novel applications of donkey-hide gelatin or deep-processed materials thereof, in particular relates to those in the preparation of compositions for improving hair quality.

BACKGROUND

According to different causative factors, hair damage can be divided into the following types: 1) physical damage: daily combing and straightening of hair, during which pulling force and friction result in the delamination and peeling off of cuticle scales covered on hair surface; 2) Chemical damage: substances such as perm agent, hair dye and decolorizer destroy the hair grease layer, and penetrate underneath the hair cuticle scales into hair cortex, causing breakage of keratin disulfide bonds, and resulting in decline of hair hydrophobicity, strength and flexibility; 3) thermal damage: hair drier or electric perm evaporates moisture, causing hair dry and brittle, broken; 4) light damage and natural aging: ultraviolet radiation in natural light causes cystine, tyrosine and tryptophan etc. photodegrade in hair keratin, and furthermore leading to hair damage and aging.

Donkey-hide gelatin is described as "sweet in taste, is to Lung, Liver and Kidney Channel Tropism". According to "Compendium of Materia Medica": "Donkey-hide gelatin is generally just complementing Xue and Qi, therefore it can clear away the Heatin the lung and enrich Yin, thereby treating various diseases . . . . Donkey-hide gelatin'ssweetness can be used to complement Yin and Xue . . . ". Donkey-hide gelatin is the captain of complementingXue, it complements Xue in five zang organs, nourishing Yin in five zang organs, it can be used for complementing various deficiencies in Xue. When blood is plentiful, hair can then be nourished and glossy. The innovation of the present invention is to utilize the function of Donkey-hide gelatin to complement blood, nourish hair and skin and make them lustrous, proposing an application of Donkey-hide gelatin or deep processed material from Donkey-hide gelatin in the production of compositions to improve hair quality. Said improvement of hair quality embodies in two aspects described below: 1) to improve the smoothness and gloss of normal hair, and promote hair growth; 2) to repair hair damage due to physical factors (such as straightening), chemical factors (such as hair coloring and de-coloring) and heating (e.g., perm). No reports have been seen on applications of Donkey-hide gelatin or deep processed material from Donkey-hide gelatin in the manufacture of compositions for improvement of the hair quality.

SUMMARY OF THE INVENTION

A first objective of the present invention is to provide an application of Donkey-hide gelatin or deep-processed substances thereof in the preparation of compositions for improving hair quality, especially in the preparation of compositions for the treatment of the following diseases, and for improving following symptoms:

Said hair quality improvements include: 1) to improve the smoothness and glossiness of normal hair, and promoting hair growth; 2) repair hair damages due to physical factors, chemical factors and the heating.

In the present invention, hair damage refers to those caused by natural or human factors resulting in following physical and chemical changes: decrease of the hair moisture content, degradation and loss of protein, leading the hair to be withered and break easily, with rough hand feeling and decreased glossiness.

The second objective of the present invention is to provide an application of Donkey-hide gelatin or deep processed materials thereof in the manufacture of compositions for promoting hair growth, or increasing hair follicle numbers.

Said Donkey-hide gelatin used in the present invention can be obtained from direct purchase from markets, or that prepared according to the existing technology and in accordance with corresponding medical-, health food- or food-standards.

In a specific embodiment of the present invention, the Donkey-hide gelatin is prepared according to the following procedure: cut soaked donkey skin into chips, place the chips into steam melt-down machine. Firstly add 1.5 times by weight of water compared to that of the donkey skin chips, heating the melt-down machine to a temperature of 117° C.-119° C., release the gelatinous juice after having kept the temperature for 120 minutes, repeat the melting-down procedure for three times, combine three released gelatinous juices, filter, centrifuge and evaporate the pooled juice. Pour the evaporated juice into a jacketed kettle (optionally, appropriate amount of rice wine, sugar and soybean oil can be added into the juice) to continue concentrating the juice into a thick paste, congeal the paste and cut the clot into pieces, dry to obtain Donkey-hide gelatin.

Said deep processed material of Donkey-hide gelatin mentioned in the present invention refers to the single materials, or mixture of multiple single materials obtained by Donkey-hide gelatin degradation, including amino acids, oligopeptides, polypeptides and proteins with molecular weights in the range of 100~350000 Da, also including new substances and mixtures of the new substances obtained by chemically modifying the single substances mentioned above.

In a specific embodiment of the present invention, deep-processed material of Donkey-hide gelatin is prepared by the following procedure: cut soaked donkey skin into chips, place the chips into steam melt-down machine. Firstly add 1.5 times by weight of water compared to that of the donkey skin chips, heating the melt-down machine to a temperature of 117° C.-119° C., release the gelatinous juice after keeping the temperature for 120 minutes, repeat the melting-down procedure for three times, combine three released gelatinous juices, filter, centrifuge and evaporate the pooled juice. Pour the evaporated juice into a jacketed kettle to continue concentrating the juice into a paste, reserved for further processing. Adjust pH of the above-mentioned Donkey-hide gelatin paste to 1.0-3.0, add pepsin to enzymatically hydrolyze the paste at a temperature of 36-42° C., subsequently inactivate the enzyme, adjust the pH to 7.5-8.5, add trypsin into the mixture to enzymatically hydrolyze the paste at a temperature of 36-42° C., subsequently inactivate the enzyme, and then ultrafilter the inactivated hydrolyzate by using a 5 KD ultrafiltration column to obtain ultra-filtrate, concentrate it at a low temperature, dry to obtain final product.

In the present invention, preferably the final concentration of added pepsin (3000 U/mg) is in the range of 0.1-0.8% (w/w), that of the added trypsin (250 U/mg) is preferably in the range of 0.1-0.8% (w/w).

Said composition mentioned in the present invention refers to a composition prepared by Donkey-hide gelatin or the deep-processed materials thereof, or those prepared by Donkey-hide gelatin or deep processed material thereof mixed with at least one kind of the material listed below:
1) one or more Traditional Chinese Medicines (TCM's);
2) one or more natural products;
3) one or more compounds;
4) one or more pharmaceutically acceptable excipients;
5) one or more food additives;
6) one or more cosmetic additives;

Wherein said natural products are general terms including constituents of animals, plants, insects, marine organisms and microorganisms or their metabolites as well as the endogenous chemical composition in human and animal. Said natural product including but not limited to the following: proteins, peptides, amino acids, nucleic acids, various enzymes, monosaccharides, oligosaccharides, polysaccharides, glycoproteins, resin, colloid, lignin, vitamins, fats, oils, waxes, alkaloids, volatile oils, flavonoids, glycosides, terpenes, phenylpropanoids, organic acids, phenols, quinones, lactones, steroids, tannins, antibiotics and other naturally occurring chemicals.

The compositions proposed in present invention may be any formulations of pharmaceutical, food or cosmetic ones, these formulations include, but are not limited to the following ones: tablets, sugar-coated tablets, film-coated tablets, enteric coated tablets, capsules, hard capsules, soft capsules, oral solutions, buccal tablets, granules, electuaries, pills, pulvis, pastes, pellet form preparations, suspensions, powders, solutions, injections, suppositories, ointments, plasters, creams, sprays, drops, patches and liniment.

Advantages of the Present Invention are:
1. The present invention provides a new medical use of Donkey-hide gelatin, exploits its new area of applications; in particular, the present invention provides an application of Donkey-hide gelatin or deep-processed material thereof in the preparation of compositions for improving hair quality, promoting hair growth and enhancing follicle numbers.
2. Donkey-hide gelatin has a distinct effect on nourishing hair, mainly for the following aspects: it can increase number and types of white blood cells in cyclophosphamide-induced anemia mice model. Results of the amino acid assays show that Donkey-hide gelatin has an effect on improving the amino acid content in animal hairs; measurements on hair growth length and the number of hair follicles show that Donkey-hide gelatin promotes hair growth and enhances the number of hair follicles.
3. The raw material of Donkey-hide gelatin is obtained from food, so it is safe to take, it has a long history of application, is suitable for those patients of different ages who want to improve their hair quality. Pharmacological tests and human trials confirm that compositions prepared from Donkey-hide gelatin or deep processed material of Donkey-hide gelatin can significantly increase the amino acid content in hair, repair damaged hair cuticles and improve hair softness and surface gloss, etc., so as to achieve the purposes of improving hair quality.

BRIEF DESCRIPTION TO THE ATTACHED FIGURES

Below are the further explanations to the present invention in conjunction with the accompanying drawing.

EMBODIMENTS

An active role played by the compositions prepared by Donkey-hide gelatin or deep processed material from Donkey-hide gelatin described in the present invention to improve the hair quality can be further confirmed by the following examples.

The following examples are only paradigmatic and do not exert any restrictions on the protective scope of the invention.

Example 1

Preparation of Donkey-Hide Gelatin

Cut soaked donkey skin into chips, place the chips into steam melt-down machine. Firstly add 1.5 times by weight of water compared to that of the donkey skin chips, heating the melt-down machine to a temperature of 117° C.-119° C., release the gelatinous juice after keeping the temperature for 120 minutes, repeat the melting-down procedure for three times, combine three released gelatinous juices, filter, centrifuge and evaporate the pooled juice. Pour the evaporated juice into a jacketed kettle (optionally, appropriate amount of rice wine, sugar and soybean oil can be added into the juice) to continue concentrating the juice into a thick paste, congeal the paste and cut the clot into pieces, and dry to obtain Donkey-hide gelatin.

Example 2

Preparation of Deep-Processed Material of Donkey-Hide Gelatin

Cut soaked donkey skin into chips, place the chips into steam melt-down machine. Firstly add 1.5 times by weight of water compared to that of the donkey skin chips, heating the melt-down machine to a temperature of 117° C.-119° C., release the gelatinous juice after keeping the temperature for 120 minutes, repeat the melting-down procedure for three times, combine three released gelatinous juices, filter, centrifuge and evaporate the pooled juice. Pour the evaporated juice into a jacketed kettle to continue concentrating the juice into a paste, reserved for further processing. Adjust pH of the above-mentioned paste to 2.0, add pepsin (3000 U/mg) to a final concentration of 0.5% (w/w), to enzymatically hydrolyzethe paste at a temperature of 42° C., subsequently inactivate the enzyme, adjust the pH to 8.0, add trypsin (250 U/mg) into the mixture to a final concentration of 0.5% (w/w), to enzymatically hydrolyze the paste at a temperature of 42° C., subsequently inactivate the enzyme, and then ultrafilter the inactivated hydrolyzate by using a 3 KD ultrafiltration column to obtain ultrafiltrate, concentrate it at a low temperature and dry to obtain deep-processed product of Donkey-hide gelatin.

Example 3

Preparation of Deep-Processed Material of Donkey-Hide Gelatin

Cut soaked donkey skin into chips, place the chips into steam melt-down machine. Firstly add 1.5 times by weight of water compared to that of the donkey skin chips, heating the melt-down machine to a temperature of 117° C.-119° C., release the gelatinous juice after keeping the temperature for 120 minutes, repeat the melting-down procedure for three times, combine three released gelatinous juices, filter, centrifuge and evaporate the pooled juice. Pour the evaporated juice into a jacketed kettle to continue concentrating the juice into a paste, reserved for further processing. Adjust pH of the above-mentioned paste to 2.5, add pepsin (3000 U/mg) to a final concentration of 0.8% (w/w), to enzymatically hydrolyze the paste at a temperature of 40° C., subsequently inactivate the enzyme, adjust the pH to 7.5, add trypsin (250 U/mg) into the mixture to a final concentration of 0.2% (w/w), to enzymatically hydrolyze the paste at a temperature of 40° C., subsequently inactivate the enzyme, and then ultrafilter the inactivated hydrolyzate by using a 5 KD ultrafiltration column to obtain ultrafiltrate, concentrate it at a low temperature and dry to obtain deep-processed product of Donkey-hide gelatin.

Test Example 1

Pharmacological Experiments

1 Materials and Animals 1.1 Materials: Donkey-hide gelatin (E-Jiao Co. Ltd., Dong-E, Shandong. Batch number: 1211037), the preparation method for this product was the same as described in Example 1; cyclophosphamide injection, (Pude Pharmaceutical Co. Ltd., Shanxi. Batch number: 04110603); rosin, paraffin and normal saline (all obtained from Qidu Pharmaceutical Co. Ltd., Shandong.Batch number: 2011112603).

1.2 Experimental animals: 120 SPF C57BL/6 female mice, 15~20 g (Fukang Biotechnology Co. Ltd., Beijing, China. Production license number: SCXK (Beijing) 2009-0004; mouse feed (Fukang Biological Technology Co. Ltd., Beijing, China. Production license number: SCXK (Beijing) 2009-0008).

1.3 Environmental conditions: Shandong Experimental Animal Center, Barrier Environment Animal Room. License number: SYXK (Lu) 20090014, environmental temperature: 20~25° C., relative humidity: 50% to 70%.

2 Methods 2.1 Solution preparation: Pulverize the Donkey-hide gelatin, dissolve the powder with appropriate amount of distilled water to prepare solutions with concentrations of 135 mg/mL, 67.5 mg/mL and 33.75 mg/mL, labeled as high-, medium-, low-dose solutions.

2.2 Pretreatment of experimental animals: Melt 1:1 mixture of rosin and paraffin, smear the melt on micedorsal skin (2×3 $cm^2$), wait until the melt solidifies, then remove the hair on the areas of the skin having been smeared with the melt.

2.3 Test groups: 24 h after depilation, 75 mice whose depilatory areas are smooth and with no skin damages are divided into five groups, denoted as high-, medium- and low-dose groups, and negative control- and model control-groups, 15 mice/group.

2.4 establish the Donkey-hide gelatin test groups and model control group, administer one-time intra peritoneal injection of 250 mg/100 g·bw cyclophosphamide, the dosage is 0.2 mL/10 g·bw; for negative control group, administer one-time intra peritoneal injection of 0.2 mL/10 g·bw normal saline.

2.5 Administration of Donkey-hide gelatin samples: each test group is given oral doses of Donkey-hide gelatin solution corresponding to a daily fed amount of 0.2 mL/10 g·bw; negative control group and model control group is orally given gavage administration of distilled water, daily gavage amount 0.2 mL/10 g·bw. Each group is continuously administered for 20 d.

2.6 Test Procedure: 24 h after pretreatment to C57BL/6 mice, pick 75 mice whose depilatory areas were smooth and with no skin damages, divide them into five groups, establish anemiamouse model, orally administer Donkey-hide gelatin as described in section 2.5. 4 d, 12 d, and 20 d after administration, respectively, collect samples of blood and skin tissue in the epilation region from each group of mice for hematologic and histopathologic tests. 20 d after administration, collect hair samples from each group of mice, for morphologic observation using electron microscope, and to examine the amino acid contents in remaining newly grown hair of each animal.

3 Results 3.1 Hematologic indices: white cells, red cells, hemoglobin, hematocrit and platelets.

3.2 Hair examination indices: length, shape, amino acid contents.

3.3 Histopathological examination: skin integrity, congestion, edema, inflammatory cell infiltration; follicle counts and statistics.

3.4 Hematology Test Results

Statistical tests carried out on the results from mouse hematologic examinations demonstrate that the leukocytes counts and categorized counts were greater in experimental groups and in negative control group than in the model control. There is significant or extremely significant difference (* $P<0.05$, ** $P<0.01$) between dose groups. The results are shown in Table 1, Table 2 and Table 3.

TABLE 1

| | Hematologic examination results in mice (after 4 d) | | | | | | | |
|---|---|---|---|---|---|---|---|---|
| Dose groups (mg/kg) | white cells $10^9$/L | Neutrophils $10^9$/L | Lymphocytes $10^9$/L | Monocytes $10^9$/L | red cells $10^{12}$/L | Hemoglobin g/L | hematocrit % | platelets $10^9$/L |
| High-dose group | 4.75 ± 0.25** | 1.55 ± 0.66* | 2.73 ± 0.72* | 0.38 ± 0.08 | 9.55 ± 0.26* | 144.33 ± 2.62** | 42.47 ± 1.25** | 316.00 ± 13.44* |

TABLE 1-continued

Hematologic examination results in mice (after 4 d)

| Dose groups (mg/kg) | white cells $10^9$/L | Neutrophils $10^9$/L | Lymphocytes $10^9$/L | Monocytes $10^9$/L | red cells $10^{12}$/L | Hemoglobin g/L | hematocrit % | platelets $10^9$/L |
|---|---|---|---|---|---|---|---|---|
| medium-dose group | 6.81 ± 0.58* | 3.11 ± 0.70 | 2.89 ± 0.50 | 0.48 ± 0.09* | 10.11 ± 0.72* | 147.33 ± 8.22* | 43.70 ± 3.47* | 534.33 ± 188.68* |
| low-dose group | 10.51 ± 2.35 | 3.74 ± 0.37 | 5.55 ± 1.65 | 0.63 ± 0.19 | 9.34 ± 0.23* | 135.0 ± 2.83 | 40.13 ± 1.02* | 499.33 ± 23.44 |
| negative control | 8.57 ± 0.89 | 3.09 ± 0.72 | 4.52 ± 1.08 | 0.49 ± 0.12 | 8.86 ± 0.16 | 131.33 ± 3.40 | 38.10 ± 0.64 | 733.33 ± 249.63 |
| model control | 4.67 ± 1.80* | 1.35 ± 0.86* | 2.54 ± 0.42* | 0.25 ± 0.09* | 8.61 ± 0.12 | 127.33 ± 1.89 | 37.63 ± 0.34 | 555.32 ± 316.92 |

Note:
The test results are expressed as mean ± standard deviation.
*P < 0.05,
**P < 0.01

TABLE 2

Hematologic examination results in mice (after 12 d)

| Dose groups (mg/kg) | white cells $10^9$/L | Neutrophils $10^9$/L | Lymphocytes $10^9$/L | Monocytes $10^9$/L | red cells $10^{12}$/L | Hemoglobin g/L | hematocrit % | platelets $10^9$/L |
|---|---|---|---|---|---|---|---|---|
| High-dose group | 10.04 ± 6.20 | 2.45 ± 1.98 | 6.40 ± 3.53 | 0.88 ± 0.80 | 8.36 ± 2.30 | 119.50 ± 30.73 | 35.95 ± 9.74 | 626.75 ± 137.02* |
| medium-dose group | 2.36 ± 3.40* | 3.60 ± 0.60** | 7.38 ± 2.56* | 1.30 ± 0.50* | 9.88 ± 0.32 | 148.25 ± 2.38 | 42.90 ± 1.10* | 780.25 ± 121.98* |
| low-dose group | 6.76 ± 1.04 | 2.00 ± 0.61 | 4.18 ± 0.62 | 0.57 ± 0.12 | 9.77 ± 0.24 | 145.40 ± 4.80 | 41.46 ± 0.94 | 752.40 ± 61.98* |
| negative control | 6.72 ± 1.33 | 1.78 ± 0.41 | 4.21 ± 0.96 | 0.66 ± 0.08 | 9.86 ± 0.23 | 147.75 ± 4.97 | 41.05 ± 1.41 | 1013.50 ± 175.37 |
| model control | 5.63 ± 2.36 | 4.45 ± 1.51* | 1.00 ± 0.79** | 0.11 ± 0.05** | 8.47 ± 0.70** | 126.25 ± 11.95* | 35.90 ± 2.94* | 1009.25 ± 66.41 |

Note:
The test results are expressed as mean ± standard deviation.
*P < 0.05,
**P < 0.01

TABLE 3

Hematologic examination results in mice (after 20 d)

| Dose groups (mg/kg) | white cells $10^9$/L | Neutrophils $10^9$/L | Lymphocytes $10^9$/L | Monocytes $10^9$/L | red cells $10^{12}$/L | Hemoglobin g/L | hematocrit % | platelets $10^9$/L |
|---|---|---|---|---|---|---|---|---|
| high-dose group | 10.46 ± 3.65 | 3.57 ± 1.66 | 5.86 ± 1.47 | 0.94 ± 0.62 | 8.69 ± 1.54* | 28.40 ± 20.81* | 39.34 ± 7.51 | 892.80 ± 163.57 |
| medium-dose group | 10.50 ± 1.80 | 2.79 ± 0.57 | 6.06 ± 0.97 | 1.38 ± 0.30* | 10.91 ± 0.51 | 163.60 ± 2.58 | 46.20 ± 1.85* | 872.00 ± 80.41 |
| low-dose group | 9.67 ± 3.09 | 2.25 ± 0.50 | 6.44 ± 2.29 | 0.91 ± 0.34 | 10.08 ± 1.08 | 149.80 ± 15.42 | 42.18 ± 4.19 | 722.20 ± 221.49 |
| negative control | 10.62 ± 1.68 | 2.76 ± 0.46 | 6.66 ± 1.05 | 0.99 ± 0.16 | 10.78 ± 0.16 | 159.20 ± 4.35 | 43.94 ± 0.80 | 839.40 ± 143.40 |
| model control | 4.71 ± 1.72** | 3.59 ± 0.98 | 0.94 ± 0.99** | 0.12 ± 0.04** | 10.99 ± 0.40 | 161.25 ± 4.71 | 44.83 ± 1.24 | 839.75 ± 94.96 |

Note:
The test results are expressed as mean ± standard deviation.
*P < 0.05,
**P < 0.01

3.5 Determination of Amino Acid Contents in Hairs

As can be seen from Table 4, in the high- and middle-dose group, the amino acid content values in animal hairs were all higher than model control.

TABLE 4

Assay results of amino acid contents in animal hairs.

| items | high-dose group | medium-dose group | low-dose group | negative control | model control |
|---|---|---|---|---|---|
| Aspartate (%) | 5.33 | 5.17 | 4.62 | 5.02 | 4.69 |
| Glutamic acid (%) | 13.5 | 13.3 | 12.3 | 12.7 | 11.6 |
| Serine (%) | 7.49 | 7.19 | 6.53 | 6.83 | 6.20 |
| Glycine (%) | 5.54 | 5.41 | 5.02 | 5.41 | 5.17 |
| Histidine (%) | 1.64 | 1.52 | 1.33 | 1.23 | 1.12 |
| Arginine (%) | 7.55 | 7.36 | 6.87 | 7.26 | 6.46 |
| Threonine (%) | 4.16 | 3.95 | 3.78 | 3.80 | 3.29 |
| Alanine (%) | 2.69 | 2.62 | 2.52 | 2.62 | 2.43 |
| Proline (%) | 5.19 | 5.20 | 4.92 | 5.27 | 4.70 |
| Tyrosine (%) | 5.84 | 5.64 | 5.37 | 5.62 | 4.83 |
| Valine (%) | 3.23 | 3.17 | 3.06 | 3.12 | 2.84 |
| Methionine (%) | 0.72 | 0.69 | 0.75 | 0.70 | 0.62 |
| Cystine (%) | 6.04 | 5.61 | 5.26 | 5.80 | 5.20 |
| Isoleucine (%) | 2.26 | 2.25 | 2.15 | 2.42 | 2.19 |
| Leucine (%) | 5.38 | 5.27 | 4.87 | 4.97 | 4.76 |
| Phenylalanine(%) | 3.88 | 3.42 | 2.61 | 3.21 | 3.10 |
| Lysine (%) | 2.99 | 2.91 | 2.58 | 2.71 | 2.63 |
| Total amino acid (%) | 83.4 | 80.6 | 74.5 | 78.7 | 71.8 |

3.6 Growth Status of Mouse Hair

Figures 1, 1A, 1B, 1C, 1D:
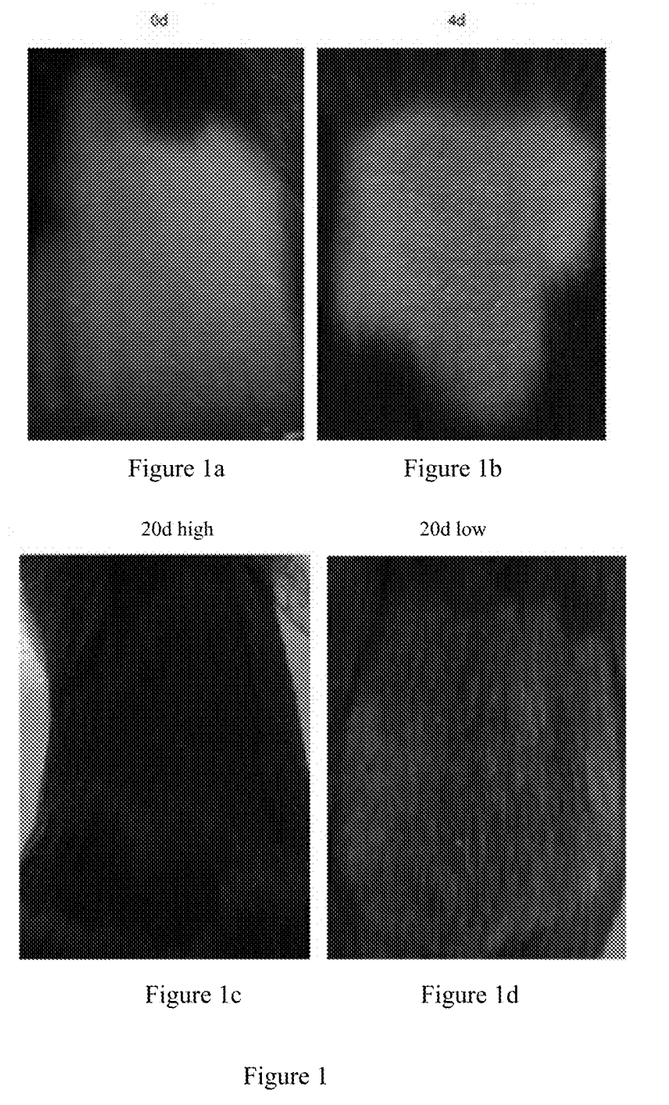
FIG. 1a-FIG. 1d are the photos of the hair growth of the test group at 0 d, 4 d, 20 d high dose, 20 d low dose Donkey-hide gelatin administration respectively.
Figure 2:
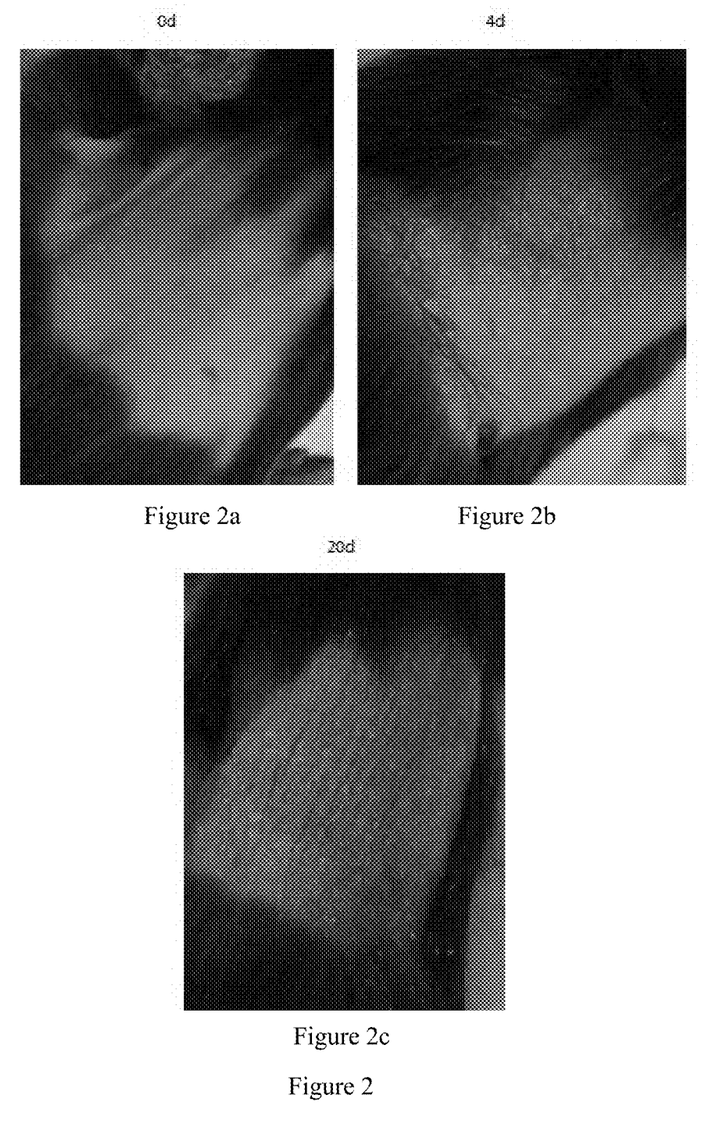
FIG. 2a-FIG. 2c are the photos of the hair growth of the model control group on 0 d, 4 d, 20 d respectively.
Figure 3A:
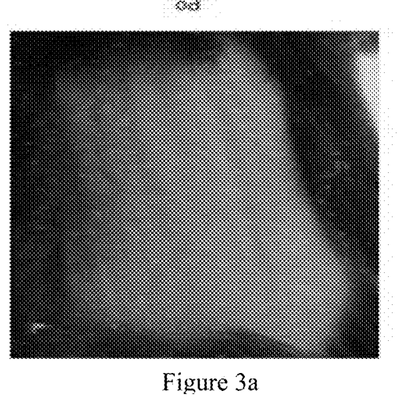
FIG. 3a-FIG. 3c are the photos of the hair growth of the negative control group on 0 d, 4 d, 20 d respectively.
Figure 3B:
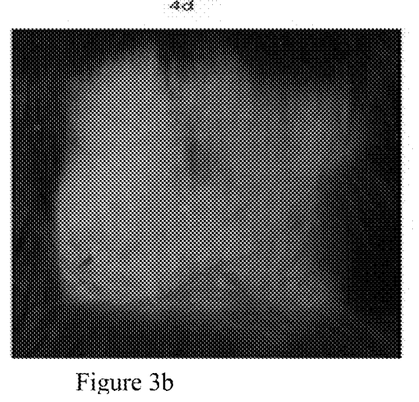
Figure 3C:
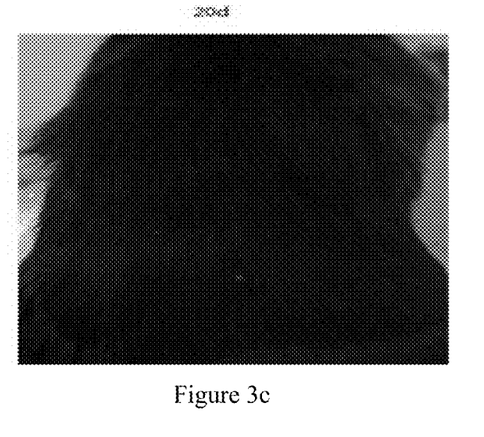

Statistical results from mouse hair length (see Table 5) and hair growth picture (see FIG. 1-FIG. 3) demonstrate that when the mice were sacrificed on $20^{th}$ day their hair lengths and densities were better than the model control but not as good as the negative control group. With respect to animal hair length there was no significant difference (P>0.05) between the test group and negative control group, there was extremely significant difference (P<0.01) between model control group and the negative control group with respect to animal hair length.

TABLE 5

Results of statistical test on mouse hair lengths (20 d)

| | Dose groups | | | | |
|---|---|---|---|---|---|
| | High-dose group | medium-dose group | low-dose group | negative control | model control |
| hair lengths (mm) | 6.10 ± 0.32 | 5.80 ± 0.70 | 5.76 ± 0.56* | 6.56 ± 0.50 | 4.04 ± 0.52** |

Note:
The test results are expressed as mean ± standard deviation (*P < 0.05, **P < 0.01)

3.7 Results of Electron Microscopic Observations

Electron microscopic observation results demonstrate that bamboo joint-like change happened in newly grown hairs in model control animals, the growth of hairs in negative control group animals were normal, differences emerged among the results of the test group animals after administration, hair diameter differences between the groups was significant; animal hairs grew nicely in negative control group. Between the experimental groups, diameters of animal hairs in high-dose group were significantly greater than those in the low-dose group; those in experimental group were significantly greater than those in model control group.

3.8 Pathological Examination Results

Figure 4:
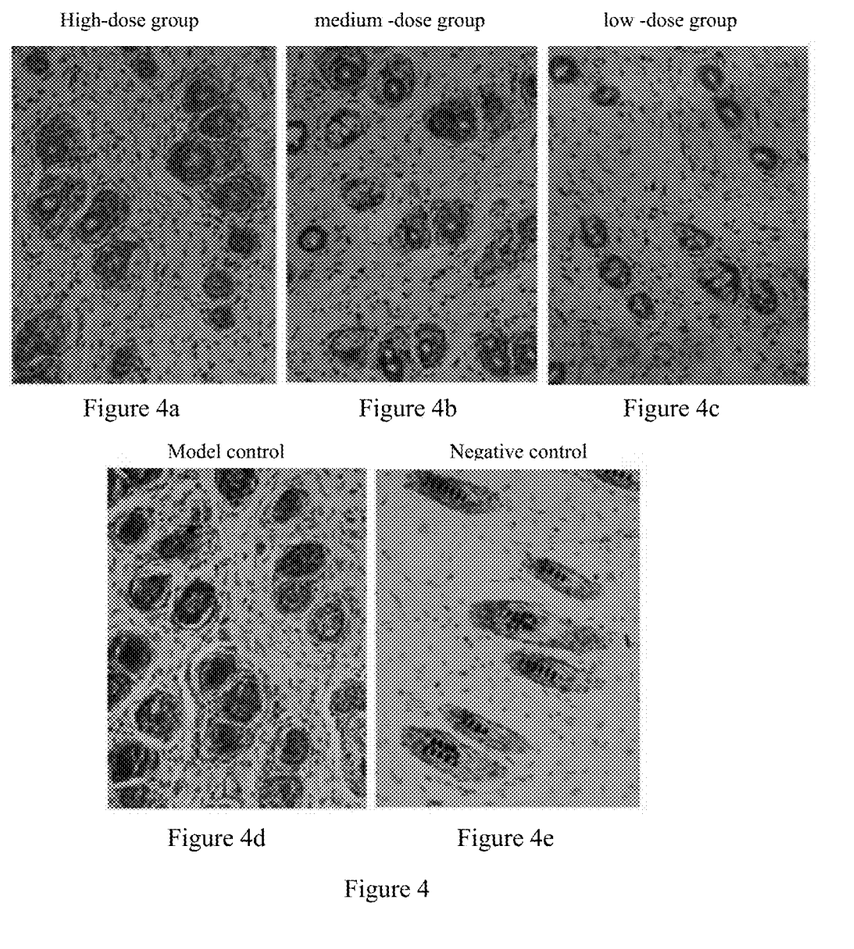
FIG. 4a-FIG. 4e are the pathological test results of mouse follicles in high Donkey-hide gelatin dose-, low-dose-, model- and control-group, respectively.

As can be seen from Table 6 and FIG. 4, the pathological observation on mice in each dose group found no congestion, edema and inflammatory cell infiltration. The statistical results of the numbers of follicles obtained from experimental animals was greater than those from model control, but less than those from negative control group. There was significant difference between the numbers of hair follicles in experimental animal groups and in negative control animals group (P<0.05), and an extremely significant difference between model control animal groups and negative control animal groups (P<0.01).

TABLE 6

Statistical results from the skin pathology examination and that on numbers of hair follicles in mice

| | Pathological Observation | | | |
|---|---|---|---|---|
| Groups | Congestion | Edema | Inflammatory cell infiltration | The numbers of follicles |
| high-dose group | 0 | 0 | 0 | 58.07 ± 6.73* |
| medium-dose group | 0 | 0 | 0 | 57.80 ± 7.04* |
| low-dose group | 0 | 0 | 0 | 57.07 ± 6.46* |
| negative control | 0 | 0 | 0 | 64.13 ± 10.90 |
| model control | 0 | 0 | 0 | 53.33 ± 9.41** |

Note:
The test results of the number of hair follicles are expressed as mean ± standard deviation.
*P < 0.05,
**P < 0.01

4 Conclusions

During the experimental process, significant differences about animals' hair growth status were observed among the groups. Animal skin darkening happened in the test group and the model control group on the $4^{th}$ day, in contrast, the skin color of the animals on the $4^{th}$ day was still pink in the negative control. In the high dose group, on $20^{th}$ day the density of hair was significantly higher than that in low-dose group and the control group, but lower than the negative control group.

The tests above showed that Donkey-hide gelatin can increase the number and types of white cells in anemia model mice induced by in vivo administration of cyclophosphamide; amino acid content assay results showed that Donkey-hide gelatin had the role of increasing amino acid contents in animal hairs; measurement results of hair length growth and the number of hair follicles showed that Donkey-hide gelatin had the role of promoting hair growth and enhancing the number of hair follicles.

In summary, from the overall analysis of test results, Donkey-hide gelatin can exert multi-aspect role in promoting hair growth in anemic mice and improving hair quality.

Test Example 2

Human Test

1 Materials and Personnel 1.1 Materials: Donkey-hide gelatin (E-Jiao Co. Ltd., Dong-E, Shandong.Batch number: 1211037); deep-processed materials of Donkey-hide gelatin was prepared using the same method described in Example 2. Batch number: 1312043.

1.2 Subjects: 30 in total, including 9 males and 27 females, with an average age of 23.6 years, they had done no hair perming, dyeing and other physical or chemical treatment in the last year. The subjects were randomly divided into control group, administration group 1 and administration group 2. Comparison of general information among the three groups showed no significant difference.

2 Method: Keep hair specimens of the subjects in three groups before the experiments. 1. After the same hair perming and dyeing treatment to the subjects in three groups, keep their hair specimens. 2. For administration group 1, orally administered Donkey-hide gelatin daily for 1 month, 9 g each day; for administration group 2, orally administered the deep processed material of Donkey-hide gelatin made according to Example 2 daily for 1 month, 6 g each day; the control group did not take any drugs. After a month, keep the hair specimens of the subjects in the three groups. 3. During the test, the subjects were not allowed to use any hair repair or hair care products. Treatment of the hair samples: collect hair, mix uniformly, wash using sodium lauryl sulfate solution, rinse cleanly, dry naturally and set aside for further test.

3 Results and Analysis 3.1 Repairing Effect on Damaged Hair Cuticles

Figure 5:
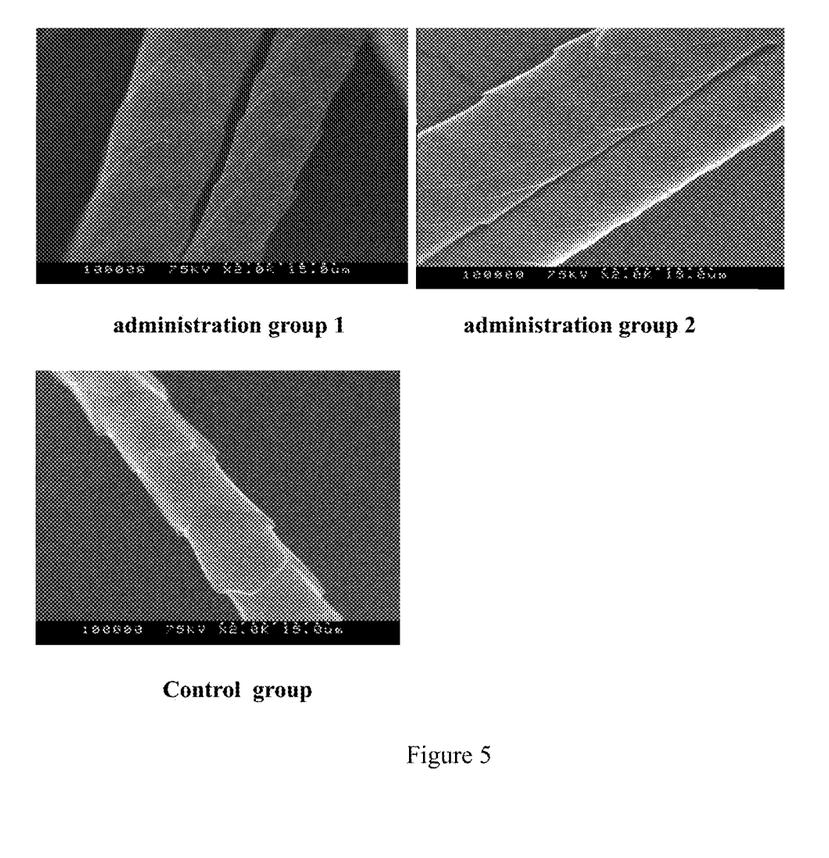
FIG. 5 are the results of scanning electron microscopic observation (×2000) on changes in the hair cuticles of the control group, administration Group 1, administration Group 2, respectively.

Scanning electron microscopy was used to observe changes in the hair cuticle, comparisons of hair electron microscopic (×2000) figures showed that diameter of the hair in control group was relatively small; whereas in administration groups 1 and 2 hair diameter was significantly greater than in the control group, and the scales on the hair distributed evenly. This meant that Donkey-hide gelatin and deep processed material thereof can improve hair quality. In the control group, bamboo joint-like hair cuticle edges tilt, even rupture, appeared, the hair surface even became rough and lost glossiness. The scales on the surface of hair in administration groups 1 and 2 distributed evenly, indicating that Donkey-hide gelatin and deep processed material thereof make hair smooth and glossy, see FIG. 5.

3.2 Determination of Hair Elasticity and Friction Coefficients 3.2.1 Hair Elasticity Experiment 10 Hair samples were measured for elasticity on an Y391 elastic yarn tester. Measurement conditions: traction was 199 g, pre-tension was 2.5 g, sample length was 50 mm. 10% of the sample lengths were taken as predetermined elongation values (Li), according to the measured value of the residual elongation (Li), calculate constant elongation elastic rate R (%) of hairs, influence of Donkey-hide gelatin administration on hair elasticity as:

$$R = 1 - \frac{\sum_{i=1}^{n} L_i}{N \cdot L_1} \times 100\%$$

Where N is the number of measurements (10 times)

3.2.2 Hair Friction Experiments

Hair static- and dynamic-friction coefficients were determined on an Y151 fiber friction tester. Results are shown in Table 7. The mass of the tension clamp was 200 mg, dynamic friction rotation speed was 30 r/min.

TABLE 7

Measurement results of hair elasticity and friction coefficients from control group, administration groups 1 and 2.

|  | Hair sample 1 | | Hair sample 2 | | Hair sample 3 | |
| --- | --- | --- | --- | --- | --- | --- |
|  | elasticity (%) | Us-Ua | elasticity (%) | Us-Ua | elasticity (%) | Us-Ua |
| Control group | 65.26 | 0.2208-0.1557 | 42.87 | 0.3041-0.2145 | 58.26 | 0.2208-0.1557 |
| administration group 1 | 66.14 | 0.2274-0.1614 | 43.75 | 0.2812-0.2275 | 78.45 | 0.1675-0.1372 |
| administration group 2 | 65.22 | 0.2189-0.1573 | 43.36 | 0.2909-0.2374 | 78.36 | 0.1649-0.1363 |

Analysis to the results: Chemical properties of hair proteins are inactive, they are relatively stable, but they are quite sensitive to heat, acids and alkali; In addition, under the effect of mechanical forces, tensile deformation will also happen. During combing and washing, especially perming and hairdressing process, hair will suffer from varying degrees of damage and destruction, the disulfide linkage in hair can be easily reduced by thiol compounds (the main component of chemical perm agent), hair surface molecular structure will be damaged, causing hairs to lose their glossiness, to be withered and easy to bifurcate, and hair elasticity and strength will also decrease, hair will become fragile and easily broken. In addition, the surface properties of an object or material are often measured by its surface coefficients of static friction (Us) and dynamic friction (Ua). If Us and Ua values are small, and the difference between the two is also small, then the surface is relatively smooth, having a soft hand feeling, glossiness is also good. A comparison between the subjects' hair qualities with or without taking Donkey-hide gelatin and deep processed material thereof, the former showed significant lower Us and Ua than the latter, which means these materials have significant effect on improving hair softness and surface glossiness. Thus, the hair becomes softer, smoother and having a better hand feeling. The smooth hair surface enhances light reflection, increases hair glossiness.

3.3 the Contents Changes of Cysteine and Tyrosine in Hair

According to the method in the literature whose topic is "Capillary electrochemical measurement of amino acids in photo damaged hair." Hui Qian, Rui Cao, Yuhua Cao, Journal of Suzhou University of Science and Technology, 2008, 25 (2): 40-43", cysteine and tyrosine in hair samples were determined, the results are cited in Table 8 below.

mol/L copper sulfate solution, it will absorb copper ions. The more is the extent of hair damage, the more is the number of negative charges carried, the more is the number of absorbed copper ions. Therefore hair damage extent can be evaluated by measuring the amount of copper ion adsorbed on it. From the results of this experiment, it can be seen that after perming and dyeing, Administration groups 1 and 2 improved their hair quality by taking Donkey-hide gelatin and deep processed material thereof, and their hair quality can basically be restored to the level before.

TABLE 8

Result of measurements on hair cysteine and tyrosine contents in control group, administration groups 1 and 2

| | Hair sample 1 | | Hair sample 2 | | Hair sample 3 | |
|---|---|---|---|---|---|---|
| | cysteine/g · g−1 | tyrosine/g · g−1 | cysteine/g · g−1 | tyrosine/g · g−1 | cysteine/g · g−1 | tyrosine/g · g−1 |
| Control group | 0.0858 ± 0.0063 | 0.0308 ± 0.0058 | 0.0558 ± 0.0074 | 0.0258 ± 0.0057 | 0.0603 ± 0.00089 | 0.0284 ± 0.0087 |
| administration group 1 | 0.0844 ± 0.0075 | 0.0288 ± 0.0036 | 0.0544 ± 0.0087 | 0.0225 ± 0.0075 | 0.0832 ± 0.0095 | 0.0277 ± 0.0066 |
| administration group 2 | 0.0839 ± 0.0082 | 0.0307 ± 0.0047 | 0.0538 ± 0.0092 | 0.0233 ± 0.0083 | 0.0828 ± 0.0093 | 0.0286 ± 0.0089 |

Analysis to the results: hair quality depends on the completeness of the hair structure and composition. Hair is subject to influence of various environmental and physico-chemical factors, causing damages, mainly those in their structure and components. In this study, capillary electro-chemical detection technologies are adopted to monitor the changes in contents of cysteine and tyrosine before and after hair perming and dyeing to evaluate the damage to the hair. Cysteine and tyrosine were measured to have a different degree of reduction after perming in this experiment, however, in the administration groups 1 and 2, after administering Donkey-hide gelatin and deep processed material thereof, hair cysteine and tyrosine contents recovered to the level before hair perming and dyeing, 3.4 Characterization of Damage to Hair by Means of the Amount of Copper Ion Adsorption by Hair According to the literature whose topic is "Evaluation of the extent of hair damage using adsorption amount of copper ions, Cheng Ruonan, Daily Chemical Industry, 2005, 35 (6): 400-402", measurement method for the amount of absorbed copper ion was established, the amount of adsorbed copper ions was used for characterizing the extent of hair damage, the results are shown in Table 9.

3.5 Typical Subject Examples

Example 1

Female, 28 years old, had brown, partially forked and dull hair. After taking Donkey-hide gelatin for a month, hair quality improved significantly, forky phenomenon disappeared; after a further perm treatment with continuation of taking Donkey-hide gelatin, hair quality improved obvious, restored to a level as before perming and dyeing.

Example 2

Female, 23 years old, hair lost severely, partially forked and dull, hair was thin and having too much hair grease, had to wash hair daily, After taking deep processed material of Donkey-hide gelatin in Example 2 for a month, the hair quality significantly improved, forked phenomenon disappears, her hair wash can be decreased to once in 3 days. Before taking Donkey-hide gelatin, hair would lose severely every time when hair was washed, this phenomenon improved after taking Donkey-hide gelatin; after a further perm treatment with continuation of taking Donkey-hide gelatin, hair quality improved obvious, restored to a level before perming and dyeing.

TABLE 9

Results of the measurements on the amounts of absorbed copper ion by hairs in control group and in Administration groups 1, 2.

| | The amounts of absorbed copper ion by hairs c/mol · L$^{-1}$ · g$^{-1}$ | | |
|---|---|---|---|
| | Hair sample 1 | Hair sample 2 | Hair sample 3 |
| Control group | $2.548 \times 10^{-2} \pm 0.515 \times 10^{-2}$ | $5.026 \times 10^{-2} \pm 1.563 \times 10^{-2}$ | $4.578 \times 10^{-2} \pm 1.627 \times 10^{-2}$ |
| administration group 1 | $2.643 \times 10^{-2} \pm 0.486 \times 10^{-2}$ | $4.947 \times 10^{-2} \pm 1.174 \times 10^{-2}$ | $2.812 \times 10^{-2} \pm 1.116 \times 10^{-2}$ |
| administration group 2 | $2.585 \times 10^{-2} \pm 0.614 \times 10^{-2}$ | $4.856 \times 10^{-2} \pm 1.085 \times 10^{-2}$ | $2.758 \times 10^{-2} \pm 1.032 \times 10^{-2}$ |

Analysis to the results: When the hair is subjected to physical or chemical damage, disulfide bonds between keratin molecules in hair are severed, so that the hair will carry negative charges. When negatively charged hair dips in 0.2

The invention claimed is:

1. A method of preparing a deep-processed material from Donkey-hide gelatin comprising:

cutting soaked donkey skin into chips, and placing the chips into a steam melt-down machine, adding 1.5 times by weight of water compared to that of the donkey skin chips into the melt-down machine, performing a melting-down procedure including heating the melt-down machine to a temperature of 117° C.-119° C., and releasing gelatinous juice from the melt-down machine after maintaining the temperature for 120 minutes, repeating the melting-down procedure for three times, and combining three released gelatinous juices, filtering, centrifuging, and evaporating the combined juices, pouring the evaporated juices into a jacketed kettle to continue concentrating the poured juices into a paste, adjusting a pH of the paste to 1.0-3.0, adding pepsin into the paste to enzymatically hydrolyze the paste at a temperature of 36-42° C., and subsequently inactivating the pepsin, adjusting the pH of the paste to 7.5-8.5, adding trypsin into the paste to enzymatically hydrolyze the paste at a temperature of 36-42° C., and subsequently inactivating the trypsin to provide an inactivated hydrolysate, ultrafiltering the inactivated hydrolyzate by using a 3 KD or 5 KD ultrafiltration column to obtain ultrafiltrate, concentrating the ultrafiltrate, and drying the concentrated ultrafiltrate to obtain a deep-processed material of Donkey-hide gelatin.

2. The method according to claim 1, wherein the pepsin is added into the paste to enzymatically hydrolyze the paste at a temperature of 36-40° C.

3. The method according to claim 1, wherein the deep-processed material of Donkey-hide gelatin includes amino acids, oligopeptides, polypeptides and proteins with molecular weights in the range of 100 to 350000 Da.

4. The method according to claim 1, further comprising using the deep-processed material of Donkey-hide gelatin to: 1) improve the smoothness and glossiness of normal hair and promote hair growth; 2) repair hair damage caused by physical factors, chemical factors and heating; or 3) promote hair growth or increase hair follicle numbers.

5. The method according to claim 1, further comprising using the deep-processed material of Donkey-hide gelatin to prepare a composition configured to improve hair quality.

6. The method according to claim 5, wherein the composition is configured to: 1) improve the smoothness and glossiness of normal hair and promote hair growth; or 2) repair hair damage caused by physical factors, chemical factors and heating.

7. The method according to claim 5, wherein the composition further includes at least one of the following kinds of materials:
1) one or more Traditional Chinese Medicines;
2) one or more natural products;
3) one or more compounds;
4) one or more pharmaceutically acceptable excipients;
5) one or more food additives; and
6) one or more cosmetic additives;
wherein said natural products include the following: proteins, peptides, amino acids, nucleic acids, various enzymes, monosaccharides, oligosaccharides, polysaccharides, glycoproteins, resin, colloid, lignin, vitamins, fats, oils, waxes, alkaloids, volatile oils, flavonoids, glycosides, terpenes, phenylpropanoids, organic acids, phenols, quinones, lactones, steroids, tannins, antibiotics and other natural chemicals.

8. The method according to claim 5, wherein the composition is prepared into a form selected from the group consisting of tablets, sugar-coated tablets, film-coated tablets, enteric coated tablets, capsules, hard capsules, soft capsules, oral solutions, buccal tablets, granules, electuaries, pills, pulvis, pastes, pellet form preparations, suspensions, powders, solutions, injections, suppositories, ointments, plasters, creams, sprays, drops, patches, and liniment.

9. The method of claim 5, wherein the composition is configured to promote hair growth or increase hair follicle numbers.

\* \* \* \* \*